United States Patent [19]

Sulkowski et al.

[11] 4,224,242
[45] Sep. 23, 1980

[54] N-[3-(LOWER)ALKYLAMINOPROPYL]-N'-(DISUBSTITUTED)PHENYLUREAS

[75] Inventors: Theodore S. Sulkowski, Wayne; James L. Bergey, Lansdale; Albert A. Mascitti, Norristown, all of Pa.

[73] Assignee: American Home Products Corporation, New York, N.Y.

[21] Appl. No.: 921,295

[22] Filed: Jul. 3, 1978

[51] Int. Cl.$^2$ .................... C07C 127/19; A61K 31/17
[52] U.S. Cl. .................... 260/553 A; 424/322
[58] Field of Search ........................... 260/553 A

[56] References Cited

U.S. PATENT DOCUMENTS

| 2,673,878 | 3/1954 | Cusic | 260/553 A |
| 2,744,930 | 5/1956 | Krapcho et al. | 260/553 A |
| 2,762,842 | 9/1956 | Hafliger et al. | 260/553 A |
| 3,140,286 | 7/1964 | Cusic et al. | 260/553 A X |
| 3,933,833 | 1/1976 | Trepanier et al. | 424/322 X |
| 4,066,695 | 1/1978 | Cohen et al. | 424/322 X |

FOREIGN PATENT DOCUMENTS 778647  7/1957  United Kingdom ................. 260/553 A

OTHER PUBLICATIONS

Dahlbom et al., CA 51:6529b (1957).
Chiti, CA 54:17409a (1960).
Koelzer et al., CA 53:22506f (1959).

Primary Examiner—Thomas A. Waltz
Attorney, Agent, or Firm—Arthur G. Seifert

[57] ABSTRACT

Compounds of the formula:

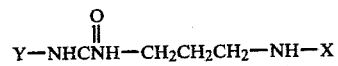

wherein:
Y is 2,6-dimethylphenyl, 2,5-dimethylphenyl, 3,5-dimethylphenyl, 2-chloro-6-methylphenyl, or 5-chloro-2-methylphenyl; and
X is methyl, ethyl, propyl, isopropyl, n-butyl, or isobutyl;

or a non-toxic, pharmaceutically acceptable acid addition salt thereof; possess anti-arrhythmic activity.

10 Claims, No Drawings

N-[3-(LOWER)ALKYLAMINOPROPYL]-N'-(DISUBSTITUTED)PHENYLUREAS

This invention relates to N-[3-(lower)alkylaminopropyl]-N'-(disubstituted)phenylureas which are useful in the treatment of cardiac arrhythmias. Heretofore the treatment of arrhythmias has been limited by drug toxicity, undesirable side effects, or variable effectiveness. Accordingly a great need exists for an anti-arrhythmic agent which is efficacious and less toxic and which has a lower incidence of undesirable side effects than known anti-arrhythmic agents.

In particular, the invention comprises chemical compounds of the formula:

wherein:
Y is 2,6-dimethylphenyl, 2,5-dimethylphenyl, 3,5-dimethylphenyl, 2-chloro-6-methylphenyl, or 5-chloro-2-methylphenyl; and
X is methyl, ethyl, propyl, isopropyl, n-butyl, or isobutyl; or a non-toxic pharmaceutically acceptable acid addition salt thereof.

The compounds of Formula I wherein X is isopropyl are preferred.

The compounds of Formula I exhibit cardiac anti-arrhythmic activity as demonstrated in laboratory tests involving a variety of arrhythmic animal models. The compounds are therefore useful in treating both atrial and ventricular arrhythmias resulting from various underlying conditions, such as ischemic heart disease, myocardial infarction, congenital cardiac defects, digitalis overdose, myocarditis, or other pathological or toxic processes which may alter the electrical excitability of the heart.

The compound of Formula I wherein Y is 2,6-dimethylphenyl and X is isopropyl offers significant advantages over known anti-arrhythmic agents because of its low toxicity, longer duration of activity, and low incidence of undesirable side effects. In particular, said compound at therapeutic doses has been found to produce little or no effect on the central nervous system (such as sedation, muscle weakness, or ataxia). Moreover, anti-cholinergic effects were not observed and undesirable cardiac effects (such as depressed cardiac contractility or cardiac output), were minimal at effective dosages.

The compounds of Formula I can be prepared by conventional synthetic methods. The preferred method is by the reaction of an appropriate disubstituted phenyl isocyanate with an N-(lower)-alkylamino-1,3-diaminopropane in an inert organic solvent, such as dichloromethane. In order to optimize the yield, the reaction should be carried out with an excess of the diaminopropane and at a low temperature. A molar ratio of about 3 to 1 (diamine to isocyanate) is preferred and a temperature of about −5° to +5° C. is desirable.

In an alternative method, an appropriate disubstituted phenyl isocyanate is first reacted with an N-protected-N'-(lower)-alkyl-1,3-diaminopropane in an inert solvent, (such as chloroform, dichloromethane, or benzene) to form the protected intermediate (II):

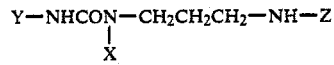

wherein Y and X have the meanings hereinbefore defined and Z is a conventional protecting group for an amino group. The protecting group is then removed to afford the deprotected intermediate III:

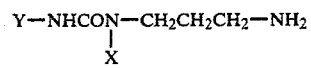

If the deprotection step is performed under the influence of heat, the intermediate (III) undergoes an intramolecular aminolysis of the amide in situ resulting in substitution of the (lower)-alkyl group (X) at the terminal position of the chain. The initial reaction between the isocyanate and the protected diamine is carried out in an inert solvent, such as chloroform, dichloromethane, or benzene. If the deprotection reaction is carried out at room temperature, the deprotected intermediate III can be isolated, and it can thereafter be converted to the final product by heating the intermediate in a suitable solvent, such as chloroform.

Protecting groups for an amino group are known in the art. Suitable groups are those which will prevent undesirable side reactions from occurring at the amino group during the initial reaction and which will be easily removed under mild conditions after the initial reaction.

Methods for making the protected amino compounds and for removing the protecting groups are well-known in the art. Preferred protecting groups are the carbobenzoxy group and the anisylidine group. The anisylidine group can be removed by treating the protected amine intermediate with hydroxylamine p-toluenesulfonate in refluxing dioxane or ethyl alcohol. Under such conditions aminolysis takes place in situ. The carbobenzoxy group can be removed by treatment with hydrogen bromide in acetic acid at room temperature. The deprotected amine (III) can be isolated and thereafter converted to the final product by mild heating.

The compounds of Formula I can be isolated in the form of the free base or in the form of a non-toxic acid addition salt prepared by reaction of the free base with a pharmaceutically acceptable organic or inorganic acid. Suitable acids will be apparent to those skilled in the art. Examples of such acids are p-toluene sulfonic (tosyl), hydrochloric, or phosphoric. The tosyl salt is preferred.

In another aspect, the invention provides a method of suppressing cardiac arrhythmias in warm-blooded animals which comprises administering to said animal orally or parenterally an effective amount of a compound of Formula I, wherein X and Y are as hereinabove defined, or a non-toxic, pharmaceutically acceptable acid addition salt thereof. The anti-arrhythmic dosage of a compound of Formula I will vary according to the particular subject being treated, the severity and nature of the arrhythmia, and the particular subject being treated. Therapy should be initiated at a low dosage, the dosage thereafter being increased until the desired anti-arrhythmic effect is obtained. In general, with large warm-blooded animals (about 70 kg. body weight) effective results can be achieved by the oral route at a daily dosage level of from about 0.5 g. to about 1.5 g. given as needed.

In yet another aspect, the invention provides a pharmaceutical composition comprising: (a) a compound of Formula I, wherein X and Y have the meanings hereinbefore defined, or a non-toxic, pharmaceutically acceptable acid addition salt thereof, and (b) a pharmaceutically acceptable carrier.

The active substnaces may be administered alone or in combination with pharmaceutically acceptable carriers, the proportion and nature of which are determined by the solubility and chemical properties of the compound selected, the chosen route of administration, and standard pharmaceutical practice. For example, the compounds of Formula I may be administered orally in solid dosage forms, e.g. capsules, tablets, or powders, or in liquid forms, e.g. solutions or suspensions. The compounds may also be injected parenterally in the form of sterile solutions or suspensions. Solid oral forms may contain conventional excipients, for instance: lactose, succrose, magnesium stearate, resins, and like materials. Liquid oral forms may contain various flavoring, coloring, preserving, stabilizing, solubilizing or suspending agents. Parenteral preparations are sterile aqueous or nonaqueous solutions or suspensions which may contain various preserving, stabilizing, buffering, solubilizing, or suspending agents. If desired, additives, such as saline or glucose may be added to make the solutions isotonic.

The following examples are illustrative of the processes of the invention. All temperatures are in centigrade.

EXAMPLE 1

N-Anisylidene-N'-isopropyl-1,3-diamine

A solution of 25 ml. of N-isopropyl-1,3-diaminopropane, 20.5 g. of p-anisaldehyde and 100 ml. of toluene was refluxed in a flask equipped with a water separator. After 4 hours the solution was cooled and extracted with water. After drying over magnesium sulfate, the solution was evaporated to dryness to obtain 34.5 g. of N-anisylidene-N'-isopropyl-1,3-diaminopropane. Infrared absorption (film) at 3300 cm.$^{-1}$, 2960 cm.$^{-1}$, 2830 cm.$^{-1}$, 1650 cm.$^{-1}$, 830 cm.$^{-1}$. Nuclear magnetic resonance spectrum (CDCl$_3$): 8.18 δ (S, 1H), 7.70 (d, 2H, J=9 Hz), 6.90 (d, 2H, J=9 Hz), 3.73 (S, 3H), 3.66 (m, 2H), 2.75 (m, 3H), 1.87 (m, 2H), 1.05 (d, 6H), 1.05 (m, 1H exchanges on deuteration.)

EXAMPLE 2

N-[3-(isopropylamino)propyl]-N'-2,6-dimethylphenyl urea

Method A

A solution of 7.4 g. of 2,6-dimethylphenylisocyanate and 50 ml. of dichloromethane was added to 12 g. of N-anisylidene-N'-isopropyl-1,3-diaminopropane dissolved in 100 ml. of dichloromethane. The solution was refluxed one-half hour, then cooled and extracted with water and with saturated sodium carbonate solution. After drying over magnesium sulfate, the dichloromethane was evaporated to dryness. The residue was dissolved in 100 ml. of ethanol. Eleven grams of hydroxylamine-p-toluenesulfonate were added and refluxed one-half hour. The solution was evaporated to dryness. The residue was triturated with hot ether, then dissolved in hot ethanol. Precipitate separated on standing. Recrystallization from ethanol afforded N-[3(isopropylamino)propyl]-N'-2,6-dimethylphenyl urea, 4-methylphenyl sulfonate, m.p. 152°–155° C.

Analysis for: $C_{15}H_{25}N_3O.C_7H_8SO_3$. Calculated: C, 60.66; H, 7.64; N, 9.65; S, 7.36. Found: C, 60.61; H, 7.85; N, 9.70; S, 7.07.

IR (KBr) 3380 cm.$^{-1}$, 3280 cm.$^{-1}$, 2650-3100 cm.$^{-1}$, 1670 cm.$^{-1}$, 1550 cm.$^{-1}$; NMR (DMSO) 8.18-8.68 δ (m, 2H, exchange with D$_2$O), 7.78 (S, 1H, exchanges with D$_2$O), 6.90-7.65 (m, 7H), 6.48 (m, 1H, exchanges with D$_2$O), 2.60-3.50 (m, 5H), 2.30 (S, 3H), 2.17 (S, 6H), 1.55-2.05 (m, 2H), 1.19 (d, 6H).

Method B

A solution of 73 g. of 2,6-dimethylphenylisocyanate and 150 ml. of dichloromethane was added to a stirred, cooled solution of 150 g. of N-isopropyl-1,3-diaminopropane in 400 ml. of dichloromethane. The temperature was kept between −3° and 3° C. during the addition. Stirring was continued at room temperature for an additional 3 hours. The mixture was extracted with water, then with a total of 500 ml. of 20% hydrochloric acid (v/v). The acid solution was made basic with saturated sodium carbonate solution. The mixture was extracted with dichloromethane. The dichloromethane solution was dried over magnesium sulfate, then evaporated to dryness. The residue was treated with p-toluenesulfonic acid to obtain the salt. Recrystallization from EtOH afforded N-[3-(isopropylamino)propyl]-N'-2,6-dimethylphenylurea, 4-methylphenyl sulfonate, m.p. 152°–154° C.

Analysis for: $C_{15}H_{25}N_3O.C_7H_8SO_3$: Calculated: C, 60.66; H, 7.64; N, 9.65; S, 7.36. Found: C, 60.53; H, 7.69; N, 9.45; S, 7.53.

Hydrochloride, m.p. 162°–164° C. (Recrystallized from EtOH/Et$_2$O).

Analysis for: $C_{15}H_{25}N_3O.HCl$. Calculated: C, 60.08; H, 8.74; N, 14.02; Cl, 11.83. Found: C, 60.02; H, 8.97; N, 14.02; Cl, 11.83.

Phosphate, m.p. 194°–196° C. (Recrystallized from EtOH).

Analysis for: $C_{15}H_{25}N_3O.H_3PO_4$: Calculated: C, 49.85; H, 7.81; N, 11.63. Found: C, 49.48; H, 7.89; N, 11.54.

EXAMPLE 3

N-[3-(n-propylamino)propyl]-N'-2,6-dimethylphenylurea

A solution of 14.7 g. of 2,6-dimethylphenylisocyanate and 50 ml. of dichloromethane was added to a stirred, cooled solution of 40 grams of N-n-propyl-1,3-diaminopropane and 350 ml. of dichloromethane. The temperature was kept between −3° and 0° C. during addition. Stirring was continued at room temperature for 45 minutes. The solution was extracted with water, then extracted with a total of 200 ml. of 20% hydrochloric acid (v/v). The acid solution was made basic with saturated sodium carbonate solution. The basic mixture was extracted with dichloromethane. The dichloromethane solution was dried over magnesium sulfate, then evaporated to dryness. The residue was treated with p-toluenesulfonic acid to obtain the salt. Recrystallization from EtOH/Et$_2$O afforded N-[3-(n-propylamino)-propyl]-N'-2,6-dimethylphenylurea, 4-methylphenylsulfonate, m.p. 157°–159° C.

Analysis for: $C_{15}H_{25}N_3O$. $C_7H_8SO_3$. Calculated: C, 60.66; H, 7.64; N, 9.65; S, 7.36. Found: C, 61.01; H, 7.47; N, 9.77; S, 7.09.

EXAMPLE 4

N-[3-(isopropylamino)propyl]-N'-(2,5-dimethylphenyl)urea

A solution of 14.7 grams of 2,5-dimethylphenylisocyanate and 50 ml. of dichloromethane was added to a stirred, cooled solution of 35 g. N-isopropyl-1,3-diaminopropane and 400 ml. of dichloromethane. The temperature was kept between −5° and 0° C. during addition. Stirring was continued at room temperature for one hour. The solution was extracted with water, then with 200 ml. of 15% hydrochloric acid (v/v). The acid extract was made basic with saturated sodium carbonate solution and extracted with dichloromethane. The dichloromethane solution was dried over magnesium sulfate, then evaporated to dryness. The residue was dissolved in ether and saturated with hydrogen chloride. The solid was separated and recrystallized from EtOH/Et$_2$O to obtain N-[3-(isopropylamino)propyl]-N'-(2,5-dimethylphenyl)urea, hydrochloride, m.p. 152°–154° C.

Analysis for: $C_{15}H_{25}N_3O \cdot HCl$. Calculated: C, 60.08; H, 8.74; N, 14.02; Cl, 11.83. Found: C, 59.97; H, 8.77; N, 14.03; Cl, 11.74.

EXAMPLE 5

N-[3-(isopropylamino)propyl]-N'-(5-chloro-2-methylphenyl)urea

A solution of 16.7 g. of 2-methyl-5-chlorophenylisocyanate and 50 ml. of dichloromethane was added to a stirred, cooled solution of 35 g. of N-isopropyl-1,3-diaminopropane and 250 ml. of dichloromethane. The temperature was kept at −5° to 0° C. during addition. Stirring was continued at room temperature for 20 minutes. The precipitated solid was separated by filtration. The filtrate was extracted with water, then with 200 ml. of 15% hydrochloric acid (v/v). The acid extract was made basic with saturated sodium carbonate solution, then extracted with dichloromethane. The dichloromethane solution was dried over magnesium sulfate, then evaporated to dryness. The residue was dissolved in ethanol and saturated with hydrogen chloride. The solution was evaporated to dryness in vacuo. The residue was triturated with ether until it solidified. The solid was recrystallized from EtOH/Et$_2$O to obtain N-[3-(isopropylamino)propyl]-N'-(5-chloro-2-methylphenyl)urea hydrochloride, m.p. 180°–183° C.

Analysis for: $C_{14}H_{22}N_3ClO \cdot HCl$. Calculated: C, 52.50; H, 7.24; N, 13.12; Cl, 22.14. Found: C, 52.41; H, 7.08; N, 13.32; Cl, 21.98.

EXAMPLE 6

N-(3-methylaminopropyl)-N'-2,6-dimethylphenylurea

A solution of 14.7 g. of 2,6-dimethylphenylisocyanate and 60 ml. of dichloromethane was added to a cooled, stirred solution of 40 g. of N-methyl-1,3-diaminopropane and 350 ml. of dichloromethane. The temperature was kept between −3° and 0° C. during addition. Stirring was continued at room temperature for 1.5 hours. The solution was extracted with water, then with 200 ml. of 20% hydrochloric acid (v/v). The acid extract was made basic with saturated sodium carbonate solution, and extracted with chloroform. The chloroform solution was dried over magnesium sulfate then evaporated to dryness. The residue was treated with p-toluenesulfonic acid to obtain the salt. Recrystallization from EtOH/Et$_2$O afforded N-(3-methylaminopropyl)-N'-2,6-dimethylphenylurea, 4-methylphenylsulfonate, m.p. 151°–153° C.

Analysis for: $C_{13}H_{21}N_3O \cdot C_7H_8SO_3$. Calculated: C, 58.94; H, 7.17; N, 10.31; S, 7.87. Found: C, 59.00; H, 7.07; N, 10.22; S, 7.89.

EXAMPLE 7

N-(3-ethylaminopropyl)-N'-2,6-dimethylphenylurea

A solution of 14.7 g. of 2,6-dimethylphenylisocyanate and 60 ml. of dichloromethane was added to a stirred, cooled solution of 40.8 g. of N-ethyl-1,3-diaminopropane and 300 ml. of dichloromethane. The temperature was kept between −5° and 0° C. during addition. Stirring was continued at room temperature for 3 hours. The solution was extracted with water, then with 200 ml. of 20% hydrochloric acid. The acid extract was made basic with saturated sodium carbonate solution and extracted with dichloromethane. The dichloromethane solution was dried over magnesium sulfate, then evaporated to dryness. The solid residue was dissolved in isopropanol and treated with p-toluenesulfonic acid to obtain the salt. Recrystallization from isopropanol afforded N-(3-ethylaminopropyl)-N'-2,6-dimethylphenylurea, 4-methylphenyl sulfonate, m.p. 161°–163° C.

Analysis for: $C_{14}H_{23}N_3O \cdot C_7H_8SO_3$. Calculated: C, 59.83; H, 7.41; N, 9.97; S, 7.61. Found: C, 59.72; H, 7.50; N, 9.88; S, 7.32.

EXAMPLE 8

N-[3-1-methylethylamino)propyl]-N'-3,5-dimethylphenylurea, 4-methylphenyl sulfonate A solution of 14.7 g. of 3,5-dimethylphenyl isocyanate and 25 ml. of dichloromethane was added to a stirred, cooled solution of 35 g. of N-isopropyl-1,3-diaminopropane and 150 ml. of dichloromethane. The temperature was kept between 0° and 5° C. during addition. Stirring was continued at room temperature for 3 hours. The solution was extracted with water, then with 200 ml. of 25% hydrochloric acid. The acid extract was made basic with saturated sodium carbonate solution and extracted with dichloromethane. The dichloromethane solution was dried over magnesium sulfate then evaporated to dryness. The residue was dissolved in ethanol and treated with p-toluene sulfonic acid to obtain the salt. Recrystallization from ethylacetate afforded N-[3-(1-methylethylamino)propyl]-N'-3,5-dimethylphenylurea, 4-methylphenyl sulfonate, m.p. 106°–9° C.

Analysis for: $C_{15}H_{25}N_3O \cdot C_7H_8SO_3$. Calculated: C, 60.66; H, 7.64; N, 9.65; S, 7.36. Found: C, 60.27; H, 7.66; N, 9.60; S, 7.24.

EXAMPLE 9

N-[3-(1-methylethylamino)propyl]-N'-(2-chloro-6-methylphenyl)-urea, 4-methylphenylsulfonate A solution of 16.7 g. of 2-chloro-6-methylphenyl isocyanate and 60 ml. of dichloromethane was added to a stirred, cooled solution of 46 g. of N-isopropyl-1,3-diaminopropane and 300 ml. of dichloromethane. The temperature was kept at 0°±3° C. during addition. Stirring was continued at room temperature for 3 hours. The solution was extracted with water, then with 200 ml. of 20% hydrochloric acid. The acid extract was made basic with saturated sodium carbonate solution and extracted with dichloromethane. The dichloromethane solution was dried over magnesium sulfate then evaporated to dryness. The residue was dissolved in ethanol and treated with p-toluenesulfonic acid to obtain the salt. Recrystallization from ethanol afforded N-[3-(1-methylethylamino)propyl]-N'-(2-chloro-6-methylphenyl)urea, 4-methylphenylsulfonate, m.p. 158°–160° C.

Analysis for: $C_{14}H_{22}N_3ClO \cdot C_7H_8SO_3$. Calculated: C, 55.31; H, 6.63; N, 9.22; Cl, 7.78; S, 7.03. Found: C, 55.22; H, 6.32; N, 9.25; Cl, 7.62; S, 7.38.

EXAMPLE 10

The suppression of arrhythmias by the compounds of Formula I can be elicited and demonstrated in the test procedures described below.

In each test, dogs of both sexes are anesthetized by administration of sodium pentobarbital injected I.V. at a dose of 35 mg/kg. Positive pressure artificial respiration with room air is utilized. Blood pressure is recorded from a femoral artery by means of a pressure transducer and oscillograph.

A. Suppression of electrical-stimulated ventricular fibrillations (fibrillatory threshold)

The "fibrillatory threshold" is the voltage at which ventricular fibrillation is produced by an external electrical stimuli delivered to the left ventrical during the repolarization phase of the myocardium. In this test, the anti-arrhythmic activity of a compound is assessed by its ability to increase the fibrillatory threshold in anesthetized dogs.

Ventricular fibrillation is produced in an anesthetized dog by stimulating the left ventricular epicardium for periods of 5 seconds with pulses of 3 msec. duration at a frequency of 60 Hz. The stimuli are applied through bipolar platinum electrodes, 3.5 mm. apart, embedded in a plastic plaque measuring 7×12 mm. which is sutured to the epicardium. The train of stimuli is triggered by the R-wave of the electrocardiogram and applied at increasing intensities (voltages) at 1 min. intervals until fibrillation occurs. The animal is defibrillated by a DC countershock and the sequence resumed after 10 min. Test drug is injected i.v. over a period of 5–10 min. Fibrillation threshold is determined before and starting at 10 min. after injection of each dose of drug. An increase in threshold of +0.75 volts is considered borderline, +1.0 volts is considered slight, +1.25 volts is considered moderate, and +2.0 or more is considered marked.

When tested by the procedure set forth above, the compounds described in Examples 2, 3, 4, 5, 6, 8, and 9 produced a moderate to marked increase in fibrillatory threshold at a dose of 10–20 mg/kg. No differences in activity were noted between the tosylate and hydrochloride salts of the compound of Example 2.

B. Suppression of ventricular arrhythmias produced by ouabain

The I.V. injection of ouabain results in ventricular arrhythmias. In this test, the anti-arrhythmic activity of a compound is assessed by its ability to restore normal sinus rhythm in ouabain-treated, pentobarbital anesthetized dogs. Ouabain is injected I.V. to an anesthetized dog in an initial dose of 50 μg/kg and then in incremental doses until a ventricular arrhythmia (multiform ventricular beats or ventricular tachycardia) is produced. A total dose of 55 to 60 μg/kg is usually sufficient to produce the arrhythmia. The test compound is then injected I.V. over approximately 3–5 min., starting 20 min. after the injection of ouabain, and the effect on the arrhythmia is observed. Drug injection is terminated when reversion to sinus rhythm is observed. In untreated dogs, the arrhythmia persists greater than 45 minutes.

When tested as set forth above, the compound of Example 2, as the tosyl salt, restored sinus rhythm in four of four dogs at a dose of 7.5±1.7 mg/kg, and, as the hydrochloride salt, restored sinus rhythm in seven of eight dogs at 6.8±1.1 mg/kg. In the remaining dog in the latter group, improvement of the arrhythmia was observed, but in view of the absence of a "p" wave in the ECG, a junctional rhythm was assigned. However, this dog received a higher than normal (70 μg/kg) dose of ouabain.

When tested as described above, compounds of Examples 3, 4, 5, 6, and 7 gave the following results:

| Compound | No. of Dogs | Dose (mg/kg) | Results |
|---|---|---|---|
| 3 | 2 | 7 | Restoration of sinus rhythm (2 dogs) |
|   | 1 | 7 | Improvement of sinus rhythm (1 dog) |
| 4 | 3 | 8 | Restoration of sinus rhythm |
| 5 | 2 | 10 | Restoration of sinus rhythm |
| 6 | 3 | 18.7 | Restoration of sinus rhythm |
| 7 | 1 | 10 | Restoration of sinus rhythm |
|   | 1 | 20 | Restoration of sinus rhythm |
|   | 1 | 10 | No result, dog died |

C. Suppression of ventricular arrhythmias produced by coronary ligation

Ligation of the left anterior descrnding coronary artery in two stages over a 20 minute period results in severe ventricular arrhythmias beginning at 5–7 hours and lasting about 48 hours. By the third day, arrhythmias spontaneously subside and normal rhythm is reestablished. The severity of the arrhythmia is greatest within 24 hours following ligation. In this test, the anti-arrhythmic activity of a test compound is assessed by the ability of the compound to restore normal sinus rhythm in the coronary ligated dog. The left anterior descending coronary artery of an anesthetized dog is ligated in two stages at the level of the atrial appendage. The animals recover from anesthesia and the test compound is administered to the conscious dog by I.V. injection or orally (via gastric tube) at 18 to 24 hours after ligation. The test compound is administered until reversion of sinus rhythm occurs or until the intended dose is given.

When tested by I.V. administration about 24 hours post ligation in the procedure set forth above, the compound of Example 2, either as the tosylate salt or the hydrochloride salt, restored complete sinus rhythm in six of six conscious dogs at a dose of 15–20 mg/kg. In two animals, additional compound was administered so that the total dose was >40 mg/kg. Although the animals appeared weaker, no deaths were observed. The compound of Example 3, restored sinus rhythm in two of two dogs at a dose of 10 mg/kg. The compound of Example 6 produced improvement (sinus and junction rhythm) in one dog at a dose of 5 mg/kg, but no further improvement was observed at higher doses up to 40 mg/kg. In another dog, improvement (junction rhythm) was observed at a dose of 20 mg/kg and sinus rhythm was restored at a dose of 40 mg/kg.

When tested in the procedure set forth above by oral administration about 24 hours post ligation, the compound of Example 2, as the tosylate salt, restored sinus rhythm at a dose of 40–50 mg/kg in eight of nine dogs. Although transient weakness appeared in several animals, no prolonged or serious side effects were observed in any of the eight dogs. At a dose of 35 mg/kg in two of three animals a high degree (85–100%) of sinus rhythm was restored with no side effects observed.

Oral administration of the compound of Example 2, as the hydrochloride salt, at a single dose of 50 mg/kg restored sinus rhythm but the compound produced general weakness and two out of eight dogs dies. Three of three dogs died at a single dose of 75 mg/kg. However, oral administration of the compound of Example 2 as the hydrochloride salt in 2 hourly divided doses totaling 50 mg/kg restored sinus rhythm with no adverse effects. In one dog, transient improvement and brief restoration of sinus rhythm was seen at an initial dose of 35 mg/kg and prolonged restoration of sinus rhythm was seen after an additional dose of 15 mg/kg. In the second dog, and initial dose of 25 mg/kg produced little improvement, but an additional dose of 25 mg/kg produced prolonged restoration of sinus rhythm.

When tested in the procedure set forth above by oral administration given about 48 hours post ligation, the compound of Example 2, as the tosylate or hydrochloride salt, restored sinus rhythm in four of five dogs at a dose of 15 mg/kg. Significant improvement was observed in one dog at this dose. When administered as either the tosylate or hydrochloride salt at a dose of 25 mg/kg, the compound of Example 2 restored sinus rhythm in six of seven dogs. Marked improvement was observed in one of the dogs at this dose, and restoration of sinus rhythm was observed in the animal after administration of an additional dose of 15 mg/kg.

I.V. administration of compound 5 restored sinus rhythm to four of four dogs at 8–20 mg/kg. Oral administration of this compound at 50 mg/kg produced sinus rhythm in the one dog tested. The duration of action was unusually long following oral administration.

D. Suppression of atrial arrhythmias produced by aconitine

Topical applications of aconitine to the right atrial appendage results in atrial arrhythmia. In this test, antiarrhythmic activity of a compound is assessed by its ability to restore sinus rhythm in anesthetized dogs suffering from arrhythmias induced by aconitine.

Dogs of both sexes are anesthetized by the I.V. administration of sodium pentobarbital (35 mg/kg). Atrial flutter or fibrillation (atrial rate >400/min) was produced by the application of aconitine nitrate (using a 5 mm$^2$ piece of filter paper saturated with a 0.5 mg/ml solution of aconitine nitrate) to the right atrial appendage in open-chest dogs. Atrial electrograms were recorded by means of a bipolar plaque electrode sutured to the atrial surface. Ventricular rate was derived from the lead II electrocardiogram. Drugs were injected I.V. approximately 20 minutes after establishment of the dysrhythmia.

When tested according to the procedure set forth above, the compound of Example 2, as the tosylate, restored sinus rhythm in four of four dogs at an average dose of 4 mg/kg.

What is claimed is:
1. A compound of the formula:

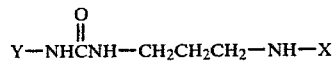

wherein:
Y is 2,6-dimethylphenyl, 2,5-dimethylphenyl, 3,5-dimethylphenyl, or 5-chloro-2-methylphenyl; and
X is ethyl, propyl, isopropyl, n-butyl, or isobutyl; or a non-toxic, pharmaceutically acceptable acid addition salt thereof.

2. A compound of claim 1 wherein X is isopropyl.
3. A compound of claim 1 wherein X is propyl.
4. The compound of claim 2 which is N-[3-(isopropylamino)propyl]-N'-2,6-dimethylphenyl urea.
5. The compound of claim 2 which is N-[3-(isopropylamino)propyl]-N'-2,6-dimethylphenyl urea, 4-methylphenyl sulfonate.
6. The compound of claim 2 which is N-[3-(isopropylamino)propyl]-N'-(2,5-dimethylphenyl)urea.
7. The compound of claim 2 which is N-[3-(isopropylamino)propyl]-N'-(5-chloro-2-methylphenyl)urea.
8. The compound of claim 1 which is N-[3-(n-propylamino)propyl]-N'-2,6-dimethylphenyl urea.
9. The compound of claim 1 which is N-(3-ethylaminopropyl)-N'-2,6-dimethylphenyl urea.
10. The compound of claim 1 which is N-[3-(isopropylamino)propyl]-N'-3,5-dimethylphenyl urea.

* * * * *